United States Patent
Hanko

(10) Patent No.: US 8,003,684 B2
(45) Date of Patent: Aug. 23, 2011

(54) CRYSTAL FORM AND PHARMACEUTICAL COMPOSITIONS OF (+)-R-ZILEUTON

(75) Inventor: Jason A. Hanko, West Lafayette, IN (US)

(73) Assignee: Cornerstone Therapeutics, Inc., Cary, NC (US)

(*) Notice: Subject to any disclaimer, the term of this patent is extended or adjusted under 35 U.S.C. 154(b) by 1126 days.

(21) Appl. No.: 11/709,299

(22) Filed: Feb. 21, 2007

(65) Prior Publication Data

US 2007/0244185 A1 Oct. 18, 2007

Related U.S. Application Data

(60) Provisional application No. 60/775,579, filed on Feb. 21, 2006.

(51) Int. Cl.
*A61K 31/381* (2006.01)
(52) U.S. Cl. .......................... 514/443; 549/58
(58) Field of Classification Search .................. 514/443; 549/58
See application file for complete search history.

(56) References Cited

U.S. PATENT DOCUMENTS 5,663,368 A 9/1997 Flisak et al.

FOREIGN PATENT DOCUMENTS

| EP | 0 279 263 A2 | 8/1988 |
| WO | WO 94/26268 | 11/1994 |

OTHER PUBLICATIONS

Brittain, Drugs and the Pharmaceutical Sciences, vol. 95, Polymorphism in Pharmaceutical Solids, 1999, Marcel Dekker, Inc. pp. 235-236 and p. 377.*
Parnes et al.; "Acute effects of antileukotrienes on sinonasal polyposis and sinusitis"; 2000; Ear, Nose & Throat Journal; 1: pp. 18, 20, 24-25.*
Chang, Zui Lin, "Zileuton," *Analytical Profiles of Drug Substances and Excipients* 25:535-575 (1998).
Cotta Ramusino, M., et al., "$^1$H NMR, UV and Circular Dichroism Study of Inclusion Complex Formation Between the 5-Lipoxygenase Inhibitor Zileuton and β- and γ-Cyclodextrins," *Journal of Inclusion Phenomena and Molecular Recognition in Chemistry* 32:485-498 (1998).
Galeazzi, E., et al., "A Congener Study of Zileuton Reveals Interesting Effects on Glucuronidation Rates," *Bioorganic & Medicinal Chemistry Letters* 4(12):1437-1442 (1994).
Rohloff, John C., et al., "Enantioselective Synthesis of 5-LO Inhibitors Using a Gulofuranose Auxiliary," *Tetrahedron Letters* 35(7):1011-1014 (1994).
International Search Report and Written Opinion for International Patent Application No. PCT/US2007/004488, dated Feb. 19, 2008, 20 pages.

* cited by examiner

*Primary Examiner* — Timothy Thomas
(74) *Attorney, Agent, or Firm* — McCarter & English LLP; Steven G. Davis

(57) ABSTRACT

Crystalline forms of (+)-R-zileuton, which may be used in pharmaceutical applications, are disclosed. Particular single crystalline forms of (+)-R-zileuton are characterized by a variety of properties and physical measurements. As well, methods of producing crystalline (+)-R-zileuton, and using it to inhibit 5-lipoxygenase activity in subjects to treat a number of diseases, are also discussed.

15 Claims, 6 Drawing Sheets

CRYSTAL FORM AND PHARMACEUTICAL COMPOSITIONS OF (+)-R-ZILEUTON

RELATED APPLICATION(S)

This application claims the benefit of U.S. Provisional Application No. 60/775,579, filed Feb. 21, 2006. The entire teachings of the above application are incorporated herein by reference.

BACKGROUND OF THE INVENTION

Zileuton ((±)-1-(1-benzo[b]thien-2-ylethyl)-1-hydroxyurea) is the active pharmaceutical ingredient in ZYFLO™, which is currently used as a treatment for asthma. ZYFLO™ is the only FDA approved asthma treatment that inhibits 5-lipoxygenase activity. 5-Lipoxygenase is responsible for the first enzymatic step in the production of leukotrienes, a family of inflammatory mediators that can trigger asthma symptoms. In addition to asthma, leukotrienes have been shown to play a role in other diseases including rheumatoid arthritis, allergic rhinitis, acne, atherosclerosis, aortic aneurysm, sickle cell disease, nasal polyposis and inflammatory bowel disease, among others. Accordingly, compounds which inhibit lipoxygenase activity are useful in the treatment and/or prevention of such diseases. Because zileuton selectively inhibits the activity of 5-lipoxygenase, it may have broader therapeutic utility than other leukotriene inhibitors.

ZYFLO is a mixture of R(+) and S(−) enantiomers of zileuton. (+)-R-zileuton is a stereoisomer of zileuton, where R denotes the absolute configuration of the molecule about its chiral center and (+) denotes the sign of rotation of plane-polarized light by the compound. Pharmaceutically active agents often exist in two or more crystalline forms that have different key physical and pharmaceutical properties including hygroscopicity, solubility, storage stability, density, hardness, flow properties and bioavailability. Crystalline forms with optimal aforementioned properties are desirable for drug production and therapeutic application.

SUMMARY OF THE INVENTION

It has been found that (+)-R-zileuton can be crystallized under well-defined conditions to provide certain crystalline forms.

One embodiment of the invention is directed towards (+)-R-zileuton, which is at least 70% by weight the single crystalline form Form I of (+)-R-zileuton described herein.

A related embodiment of the invention is a method for preparing the single crystalline form Form I of (+)-R-zileuton comprising dissolving (+)-R-zileuton in methanol and evaporating the methanol from the solution.

Another embodiment of the invention is a pharmaceutical composition comprising a pharmaceutically acceptable carrier or diluent and (+)-R-zileuton. (+)-R-zileuton is at least 70% by weight crystalline. More particularly, the (+)-R-zileuton of the pharmaceutical composition is at least 70%, 80%, 90%, 99% or 99.9% by weight a single crystalline form of (+)-R-zileuton.

Another embodiment of the invention is a pharmaceutical composition comprising a pharmaceutically acceptable carrier or diluent and (+)-R-zileuton, wherein the (+)-R-zileuton is at least 70% by weight the specific crystalline form Form I of (+)-R-zileuton described herein. More particularly, the (+)-R-zileuton of the pharmaceutical composition is at least 70%, 80%, 90%, 99% or 99.9% by weight the specific crystalline form Form I of (+)-R-Zileuton.

A related embodiment of the invention is a pharmaceutical composition comprising a pharmaceutically acceptable carrier or diluent and (+)-R-zileuton, wherein the (+)-R-zileuton is at least 70% by weight the specific crystalline form Form II of (+)-R-zileuton described herein. More particularly, the (+)-R-zileuton of the pharmaceutical composition is at least 70%, 80%, 90%, 99% or 99.9% by weight the specific crystalline form Form II of (+)-R-zileuton.

Embodiments of the invention are also directed towards a method of treating a condition characterized by increased lipoxygenase activity and/or leukotriene levels in a subject in need thereof by administering to the subject an effective amount of (+)-R-zileuton, which is at least 70% by weight crystalline (+)-R-zileuton. In another embodiment, the invention is directed to a method of treating an inflammatory condition in a subject in need thereof comprising administering to the subject an effective amount of (+)-R-zileuton, which is at least 70% by weight crystalline (+)-R-zileuton.

DETAILED DESCRIPTION OF THE INVENTION

Figure 1:
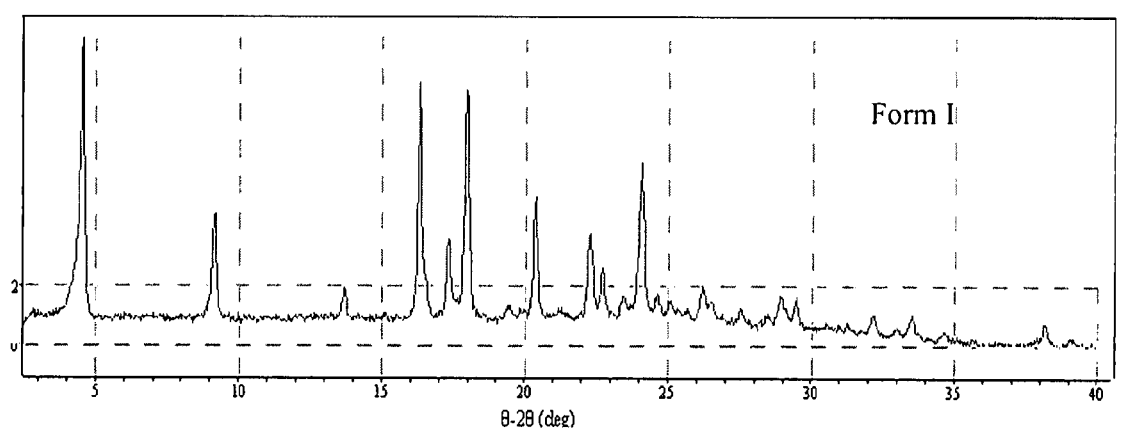
FIG. 1 is an XRPD pattern obtained from a sample of Form I of (+)-R-zileuton.

The present invention provides a unique crystalline form of (+)-R-zileuton and new pharmaceutical compositions of (+)-R-zileuton comprising the crystalline forms of (+)-R-zileuton described herein. The present invention also provides methods of treating a condition characterized by increased lipoxygenase activity and/or leukotriene levels in a subject in need thereof. Additionally, the present invention provides methods for preparing the specific crystalline forms Form I and Form II of (+)-R-zileuton. The chemical structure of (+)-R-zileuton is given by the following structural formula (I):

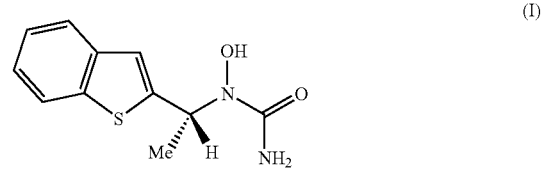

(I)

In a particular embodiment of the invention, at least a particular percentage by weight of (+)-R-zileuton is the single crystalline form Form I of (+)-R-zileuton. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%.

As used herein, "crystalline" refers to a solid having a highly regular chemical structure. Crystalline (+)-R-zileuton can be a single crystalline form of (+)-R-zileuton, or a mixture of different single crystalline forms. A single crystalline form means (+)-R-zileuton as a single crystal or a plurality of crystals in which each crystal has the same crystal form.

When a particular percentage by weight of (+)-R-zileuton is a single crystalline form, the remainder of (+)-R-zileuton is some combination of amorphous (+)-R-zileuton, and/or one or more crystalline forms of (+)-R-zileuton excluding the single crystalline form. When the crystalline (+)-R-zileuton is defined as one particular form of (+)-R-zileuton, the remainder is made up of amorphous form and/or crystalline forms other than the one or more particular forms that are specified. Examples of a single crystalline form include Forms I and II of (+)-R-zileuton, as well as descriptions of a single crystalline form characterized by one or more properties as discussed herein.

In another embodiment of the invention, a pharmaceutical composition comprises a pharmaceutically acceptable carrier or diluent and crystalline (+)-R-zileuton. More particularly, the crystalline (+)-R-zileuton is a single crystalline form. The crystalline (+)-R-zileuton or the single crystalline form of (+)-R-zileuton is at least a particular percent by weight of a total amount of (+)-R-zileuton. Particular percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%.

A related embodiment of the invention is directed to a pharmaceutical composition comprising a pharmaceutically acceptable carrier or diluent and (+)-R-zileuton, wherein at least a particular percentage by weight of (+)-R-zileuton is a specific single crystalline form as discussed herein. In one embodiment, the single crystalline form is Form I of (+)-R-zileuton. In another embodiment, the single crystalline form is Form II of (+)-R-zileuton. Particular percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%.

In the following description of particular crystalline forms of (+)-R-zileuton, embodiments of the invention may be described with reference to a particular crystalline "Form" of (+)-R-zileuton. However, the particular crystalline forms of (+)-R-zileuton may also be characterized by one or more of the characteristics of the crystalline forms as described herein, with or without regard to referencing a particular "Form".

Form I

In one embodiment of the invention, a single crystalline form of (+)-R-zileuton is characterized as Form I. This crystalline form is also characterized by the X-ray powder diffraction (herein referred to as "XRPD") pattern shown in FIG. 1 with values of 2θ angles, d-spacings and relative intensities as listed in Table 1, obtained using Cu Kα radiation. In a particular embodiment of the invention, the crystalline form is characterized by one, two, three, four or five major XRPD peaks at 2θ angles of 17.3°, 17.9°, 20.3°, 22.2° and 24.0°. In an even more particular embodiment of the invention, the crystalline form is characterized by XRPD peaks at 2θ angles of 4.5°, 9.1°, 16.3°, 17.3°, 17.9°, 20.3°, 22.2°, 22.7° and 24.0°. It is to be understood that a specified 2θ angle means the specified value ±0.1°.

As used herein, "major XRPD peak" refers to an XRPD peak with a relative intensity greater than 25%. Relative intensity is calculated as a ratio of the peak intensity of the peak of interest versus the peak intensity of the largest peak.

TABLE 1

| XRPD Peaks from FIG. 1 | | |
|---|---|---|
| 2θ angle (°) | d value (Å) | Intensity % |
| 4.1 | 21.7 | 10 |
| 4.5 | 19.5 | 100 |
| 9.1 | 9.7 | 38 |
| 13.7 | 6.5 | 11 |
| 16.3 | 5.4 | 83 |
| 16.6 | 5.3 | 9 |
| 17.3 | 5.1 | 30 |
| 17.6 | 5.0 | 7 |
| 17.9 | 4.9 | 85 |
| 19.4 | 4.6 | 5 |
| 19.8 | 4.5 | 3 |
| 20.0 | 4.4 | 3 |
| 20.3 | 4.4 | 46 |
| 21.2 | 4.2 | 3 |
| 22.2 | 4.0 | 32 |
| 22.7 | 3.9 | 17 |
| 23.4 | 3.8 | 7 |
| 24.0 | 3.7 | 56 |
| 24.6 | 3.6 | 8 |
| 25.0 | 3.6 | 7 |
| 25.6 | 3.5 | 4 |
| 26.2 | 3.4 | 13 |
| 26.5 | 3.4 | 7 |
| 27.5 | 3.2 | 6 |
| 28.4 | 3.1 | 4 |
| 28.7 | 3.1 | 5 |
| 28.9 | 3.1 | 13 |
| 29.1 | 3.1 | 6 |
| 29.4 | 3.0 | 12 |
| 31.2 | 2.9 | 3 |
| 32.1 | 2.8 | 8 |
| 33.0 | 2.7 | 4 |
| 33.4 | 2.7 | 9 |
| 34.6 | 2.6 | 4 |
| 37.9 | 2.4 | 3 |
| 38.1 | 2.4 | 9 |
| 39.0 | 2.3 | 3 |

Figure 2:
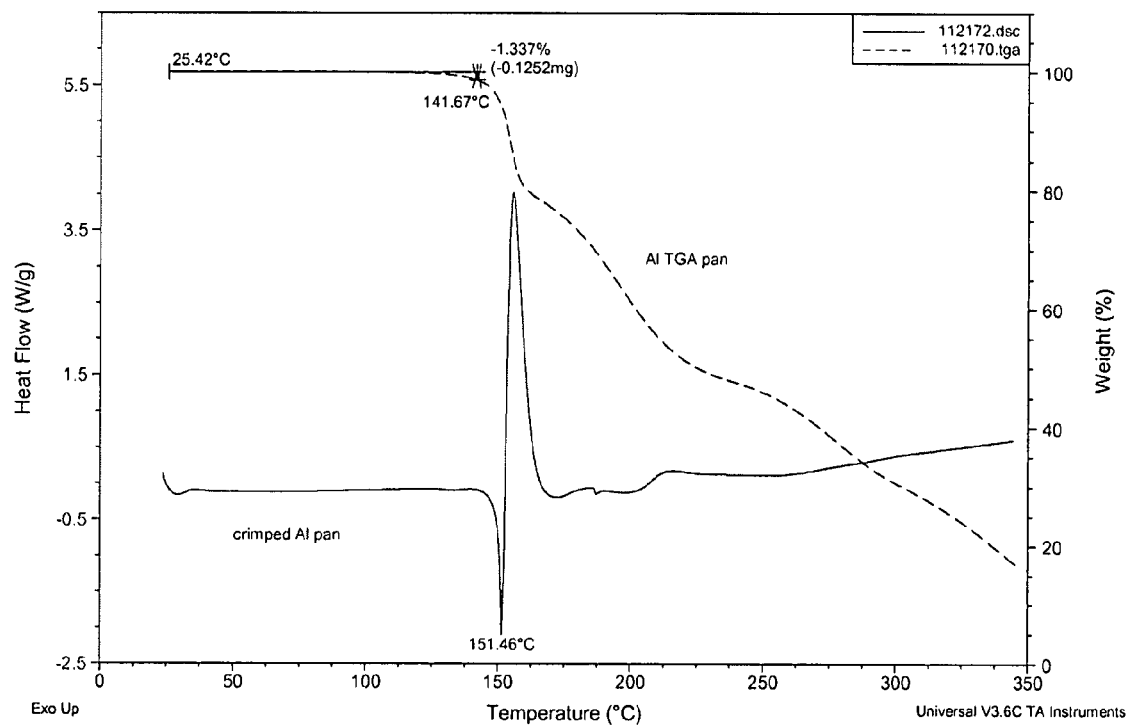
FIG. 2 is a thermal analysis profile obtained from a sample of Form I of (+)-R-zileuton, determined by DSC and TGA measurements.

In another embodiment of the invention, Form I of (+)-R-zileuton is characterized by a single endothermic transition at 151±0.5° C. in the differential scanning (herein referred to as "DSC") profile shown in FIG. 2. The profile plots the heat flow as a function of temperature from a sample containing Form I. The DSC is performed on the sample using a scanning rate of 10° C./minute. The endothermic transition observed in the DSC profile was confirmed to be a melting transition at a temperature between 138-146.4° C. by hot stage microscopy (in which the sample was heated slowly and the material recrystallized on cooling).

Figure 3:
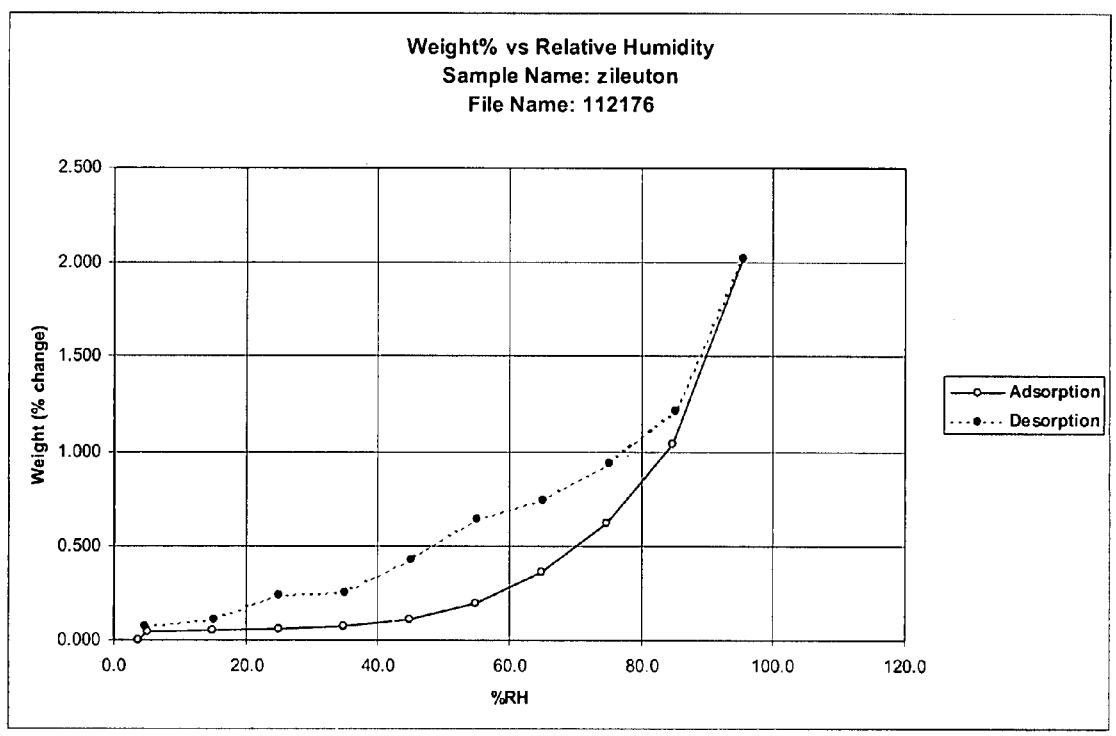
FIG. 3 is a moisture sorption/desorption profile obtained from a sample of Form I of (+)-R-zileuton.

Form I is also characterized by moisture sorption/desorption profiles shown in FIG. 3. The profiles show the change in weight of a sample containing Form I as the relative humidity (herein referred to as "RH") of the environment is changed between 5% and 95% at a 10% RH interval. The adsorption profile shows essentially no weight change at a RH below 40%, followed by a steady weight gain of approximately 2% until the RH reaches 95%. The desorption profile shows a complete weight loss with a hysteresis loop. The vapor sorption/desorption profiles indicate that Form I is non-hygroscopic.

Form I is also characterized by the thermal gravimetric analysis (herein referred to as "TGA") profile shown in FIG. 2. The profile graphs the percent loss of weight of the sample as a function of temperature with the temperature rate change being 10° C./minute. The profile shows a weight loss of approximately 1.3% as the temperature of the sample is changed from room temperature to 142° C., which indicates that Form I is anhydrous.

Form II

In an embodiment of the invention, a single crystalline form of (+)-R-zileuton is characterized as Form II. This crystalline form is also characterized by the X-ray powder diffraction (XRPD) pattern shown in FIG. 4 with values of 2θ angles, d-spacings and relative intensities as listed in Table 1, obtained using Cu Kα radiation. In a particular embodiment of the invention, the crystalline form is characterized by one, two, three, four, five or six major XRPD peaks at 2θ angles of 17.6°, 18.6°, 19.9°, 21.3°, 23.4° and 23.7°. In an even more particular embodiment of the invention, the crystalline form is characterized by XRPD peaks at 2θ angles of 4.6°, 9.2°, 16.3°, 17.6°, 18.6°, 19.9°, 21.3°, 23.4° and 23.7°.

TABLE 2

Figure 4:
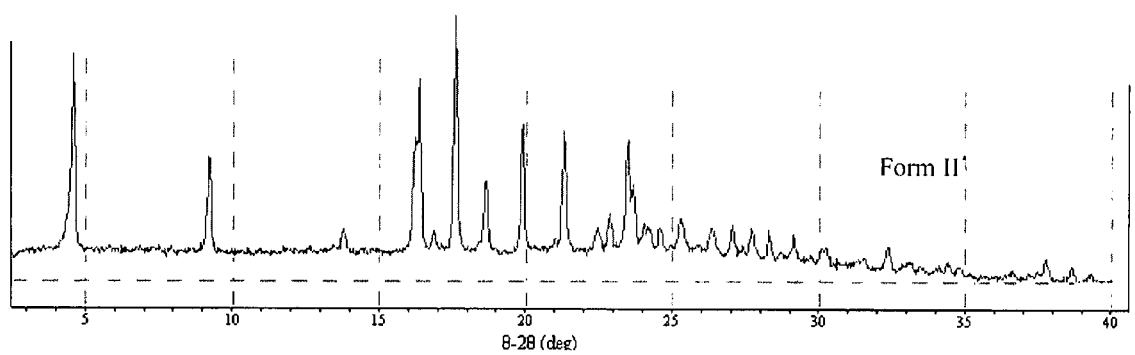
FIG. 4 is an XRPD pattern obtained from a sample of Form II of (+)-R-zileuton.

XRPD Peaks from FIG. 4

| 2θ angle (°) | d value (Å) | Intensity % |
|---|---|---|
| 4.2 | 21.3 | 4 |
| 4.3 | 20.5 | 12 |
| 4.6 | 19.4 | 78 |
| 9.2 | 9.6 | 40 |
| 13.8 | 6.4 | 10 |
| 16.1 | 5.5 | 39 |
| 16.3 | 5.4 | 72 |
| 16.8 | 5.3 | 7 |
| 17.6 | 5.0 | 100 |
| 18.3 | 4.8 | 3 |
| 18.6 | 4.8 | 31 |
| 19.9 | 4.5 | 58 |
| 21.0 | 4.2 | 6 |
| 21.3 | 4.2 | 54 |
| 21.5 | 4.1 | 3 |
| 22.4 | 4.0 | 9 |
| 22.8 | 3.9 | 16 |
| 23.4 | 3.8 | 48 |
| 23.7 | 3.8 | 29 |
| 24.0 | 3.7 | 10 |
| 24.2 | 3.7 | 10 |
| 24.6 | 3.6 | 11 |
| 25.3 | 3.5 | 14 |
| 25.5 | 3.5 | 3 |
| 25.8 | 3.4 | 3 |
| 26.3 | 3.4 | 12 |
| 27.0 | 3.3 | 13 |
| 27.4 | 3.3 | 4 |
| 27.7 | 3.2 | 13 |
| 28.3 | 3.2 | 11 |
| 29.1 | 3.1 | 11 |
| 29.7 | 3.0 | 3 |
| 30.0 | 3.0 | 6 |
| 30.2 | 3.0 | 7 |
| 31.5 | 2.8 | 5 |
| 32.3 | 2.8 | 11 |
| 33.1 | 2.7 | 5 |
| 34.0 | 2.6 | 3 |
| 34.3 | 2.6 | 6 |
| 34.8 | 2.6 | 5 |
| 37.4 | 2.4 | 3 |
| 37.7 | 2.4 | 10 |
| 38.6 | 2.3 | 7 |
| 39.3 | 2.3 | 4 |

Figure 5:
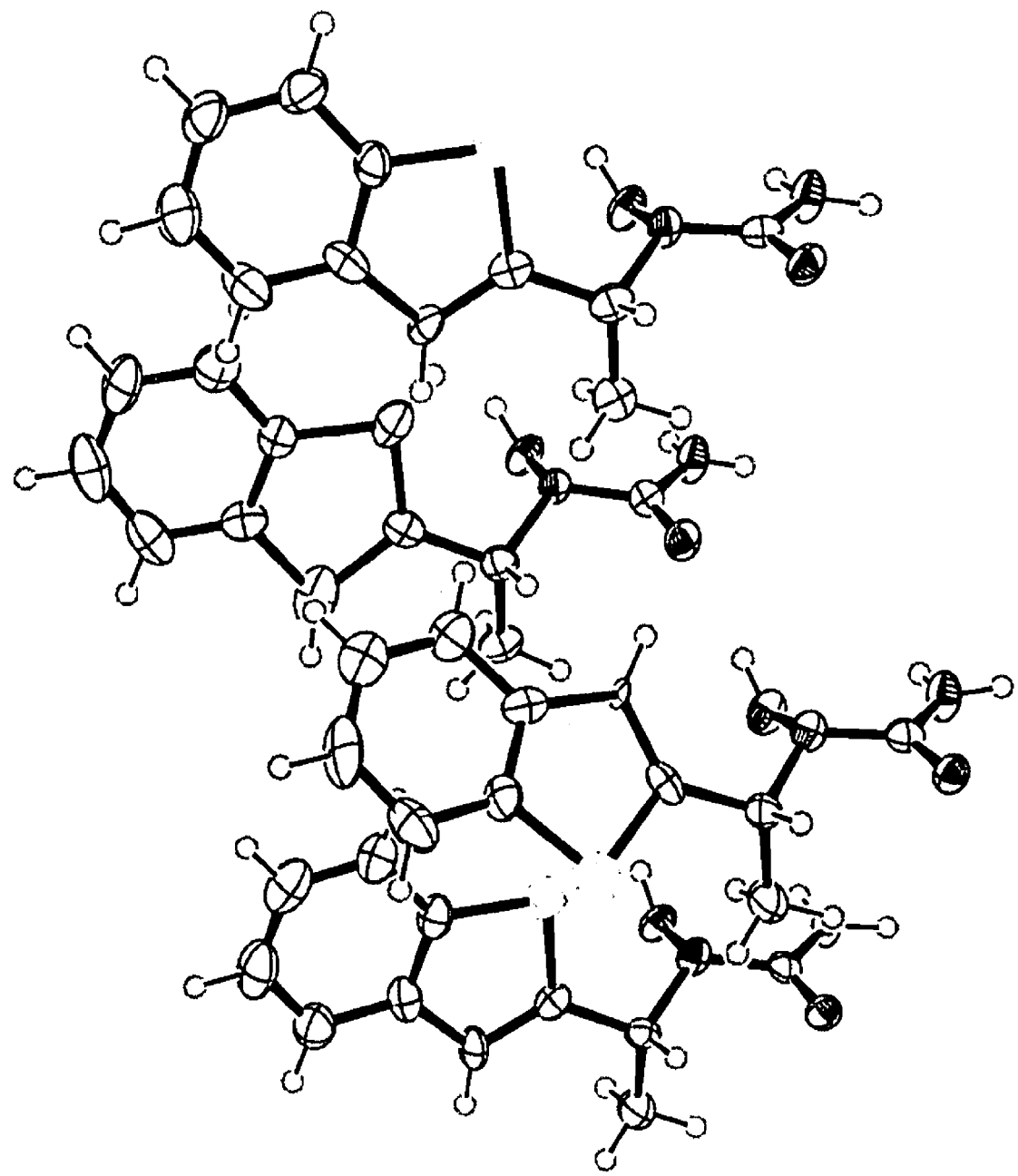
FIG. 5 is an ORTEP representation for the asymmetric unit cell structure of Form II of (+)-R-zileuton.
Figure 6:
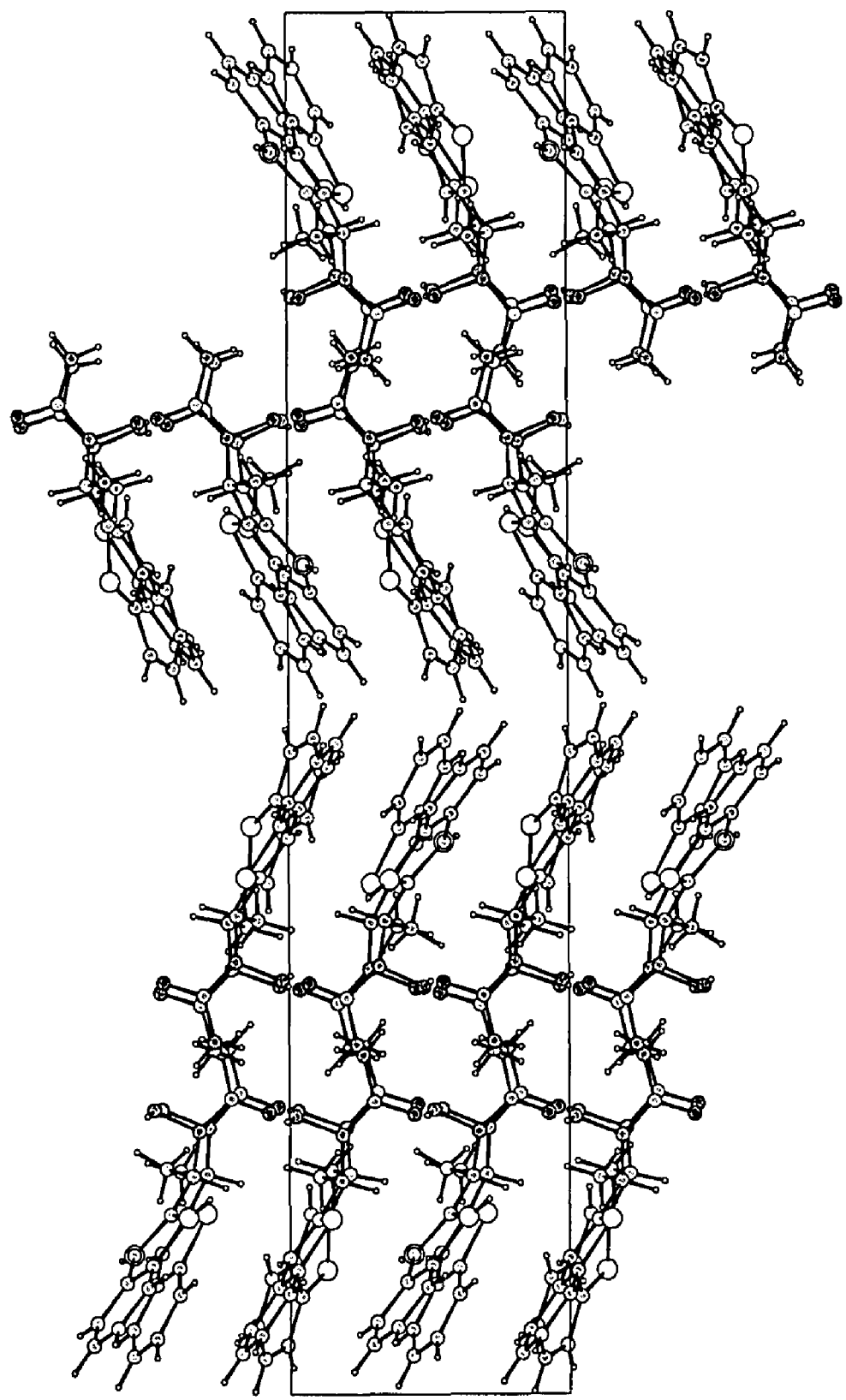
FIG. 6 is an x-ray crystallographic packing diagram for Form II of (+)-R-zileuton.

In another embodiment of the invention, Form II of (+)-R-zileuton is characterized by a single crystal structure. The single crystal structure is derived from X-ray crystallographic data obtained from suitable single crystals of Form II of (+)-R-zileuton using Mo Kα radiation. The crystal structure is characterized as a $P2_12_12_1$ space group. In a related embodiment of the invention, Form II of (+)-R-zileuton is characterized by an asymmetric unit cell structure with cell parameters listed in Table 3. The unit cell structure is also characterized by an Oak Ridge Thermal Ellipsoid Plot (ORTEP) drawing shown in FIG. 5. The unit cell consists of four zileuton molecules. Two of the (+)-R-zileuton molecules are essentially identical, while a third molecule has the benzothiophene moiety rotated approximately 180°. The fourth molecule has the sulfur atom disordered over the two possible sites in the benzothiophene moiety. In a particular embodiment of the invention, the crystalline Form II is also characterized by a packing pattern shown in FIG. 6. The packing pattern consists of alternating double layers of zileuton molecules. The packing pattern maximizes the hydrogen bonding interactions between zileuton molecules by concentrating the hydrophilic portion of the molecule.

TABLE 3

Unit Cell Parameters from Single Crystal Structure Determination of Form II of (+)-R-zileution a = 7.8840(2) Å
b = 15.0094(3) Å
c = 38.3171(10) Å
α = 90.00°
β = 90.00°
γ = 90.00°
V = 4534.22(19) Å³

As used herein, "unit cell" refers to the smallest structural component of a crystal, which is tiled in three-dimensional space to describe the crystal.

As used herein, "space group" refers to the mathematical description of the inherent symmetry of a crystal structure.

As used herein, a "packing pattern" refers to a pattern, by which the unit cell is stacked in three-dimension space to form the crystal.

Form II is also characterized as being anhydrous confirmed by the single crystal structure analysis described above.

Other embodiments of the invention are directed to a single crystalline form of (+)-R-zileuton characterized by a combination of the aforementioned characteristics of any of the single crystalline forms discussed herein. The characterization can be any combination of one or more of the XRPD, TGA, DSC, moisture sorption/desorption measurements and single crystal structure determination described for a particular crystalline form. For example, the single crystalline form of (+)-R-zileuton can be characterized by any combination of the XRPD results regarding the 2θ position of the major peaks in an XRPD scan; and/or any combination of one or more of the unit cell parameters derived from data obtained from the single crystal structure analysis. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of anhydrous (+)-R-zileuton as determined by moisture sorption/desorption measurements over a range of relative humidity can also characterize a single crystalline form of (+)-R-zileuton.

Examples of combinations of single crystalline form characterizations using multiple analytical techniques include the 2θ positions of at least one of the major peaks of an XRPD scan and the temperature associated with the maximum heat flow during one or more heat flow transitions observed by a corresponding DSC measurements; the 2θ positions of at least one of the major peaks of an XRPD scan and one or more weight losses associated with a sample over a designated temperature range in a corresponding TGA measurement; the 2θ positions of at least one of the major peaks of an XRPD scan, and the temperature associated with the maximum heat flow during one or more heat flow transitions observed by a corresponding DSC measurements, and one or more weight losses associated with a sample over a designated temperature range in a corresponding TGA measurement; the 2θ positions of at least one of the major peaks of an XRPD scan, and the temperature associated with the maximum heat flow during one or more heat flow transitions observed by a corresponding DSC measurements, one or more weight losses associated with a sample over a designated temperature range in a corresponding TGA measurement, and the change in sorption/desorption measurements over a range of relative humidity. As well, each of the aforementioned examples can replace the use of 2θ positions of at least one of the major peaks of an XRPD scan with one or more unit cell parameters of the single crystalline form.

The combinations of characterization that are discussed above can be used to describe any of the single crystalline forms of (+)-R-zileuton (e.g. Form I or II).

In another embodiment of the invention, a pharmaceutical composition comprises a pharmaceutically acceptable carrier or diluent; and crystalline (+)-R-zileuton or a single crystalline form of (+)-R-zileuton. The pharmaceutical compositions described herein can optionally include one or more pharmaceutically acceptable excipients. Such pharmaceutically acceptable excipients are well known in the art and include, for example, salts (such as protamine sulfate, disodium hydrogen phosphate, potassium hydrogen phosphate, sodium chloride, zinc salts, colloidal silica and magnesium trisilicate), surfactant(s), water-soluble polymers (such as polyvinyl pyrrolidone, cellulose based substances, polyethylene glycol, polyacrylates, sodium carboxymethylcellulose, waxes and polyethylene-polyoxypropylene-block polymers), preservatives, antimicrobials, antioxidants, cryo-protectants, wetting agents, viscosity agents, tonicity modifying agents, levigating agents, absorption enhancers, penetration enhancers, pH modifying agents, muco-adhesive agents, coloring agents, flavoring agents, diluting agents, emulsifying agents, suspending agents, solvents, co-solvents, buffers (such as phosphates, glycine, sorbic acid, potassium sorbate and partial glyceride mixtures of saturated vegetable fatty acids), serum proteins (such as human serum albumin), ion exchangers and combinations of these excipients.

The excipient included within the pharmaceutical compositions of the invention is chosen based on the expected route of administration of the composition in therapeutic applications. Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Solid dosage forms, such as tablets, pills and capsules, may also contain one or more binding agents, filling agents, suspending agents, disintegrating agents, lubricants, sweetening agents, flavoring agents, preservatives, buffers, wetting agents, disintegrants, effervescent agents, and other excipients. Such excipients are known in the art. Examples of filling agents are lactose monohydrate, lactose anhydrous, and various starches. Examples of binding agents are various celluloses and cross-linked polyvinylpyrrolidone, microcrystalline cellulose, and silicified microcrystalline cellulose (SMCC). Suitable lubricants, including agents that act on the flowability of the powder to be compressed, are colloidal silicon dioxide, talc, stearic acid, magnesium stearate, calcium stearate, and silica gel. Examples of sweeteners are any natural or artificial sweetener, such as sucrose, xylitol, sodium saccharin, cyclamate, aspartame, and accsulfame K. Examples of flavoring agents are bubble gum flavor, fruit flavors, and the like. Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride. Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, lactose such as lactose monohydrate, lactose anhydrous, dibasic calcium phosphate, mannitol, starch, sorbitol, sucrose and glucose. Suitable disintegrants include corn starch, potato starch, and modified starches, crosspovidone, sodium starch glycolate, and mixtures thereof. Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propyl parabens as preservatives, a dye and a flavoring such as cherry or orange flavor, and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administer to a wound site.

The compositions of the present invention can be administered parenterally such as, for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" is also meant to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

In another embodiment of the invention, an effective amount of (+)-R-zileuton is administered to a subject in need of 5-lipoxygenase inhibition. Alternatively, an effective amount of (+)-R-zileuton is administered to a subject with a condition caused by elevated levels of leukotrienes. (+)-R-zileuton includes a crystalline (+)-R-zileuton, or a single crystalline form of (+)-R-zileuton, described herein. Inhibiting excessive production of leukotrienes and/or 5-lipoxygenase activity may serve to treat a number of diseases including, but not limited to, asthma, ulcerative colitis, rheumatoid arthritis, psoriasis or allergic rhinitis, adult respiratory distress syndrome, acne, atherosclerosis, multiple sclerosis, nasal polyposis, sickle cell disease, acute lung injury, chronic obstructive pulmonary disease, aortic aneurysm, ischemia/reperfusion injury, gout, atopic dermatitis, irritable bowel disease, cancer, tumors, respiratory syncitial virus, sepsis, endotoxic shock and myocardial infarction.

In one embodiment, the condition mediated by lipoxygenase and/or leuktoriene activity is an inflammatory condition. Inflammatory conditions include, but are not limited to, appendicitis, peptic, gastric or duodenal ulcers, peritonitis, pancreatitis, acute or ischemic colitis, diverticulitis, epiglottitis, achalasia, cholangitis, cholecystitis, hepatitis, inflammatory bowel disease (including, for example, Crohn's disease and ulcerative colitis), enteritis, Whipple's disease, asthma, chronic obstructive pulmonary disease, acute lung injury, ileus (including, for example, post-operative ileus), allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididyinitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome, or Hodgkins disease.

In a further embodiment, the inflammatory condition is selected from the group consisting of rheumatoid arthritis, asthma, chronic obstructive pulmonary disease, acute lung injury, inflammatory bowel disease, allergy, organ ischemia, reperfusion injury, rhinitis, dermatitis, atherosclerosis, myocardial ischemia and adult respiratory distress syndrome.

Treatment including therapeutic and prophylactic treatment.

An "effective amount" refers to an amount effective to inhibit development of, or to alleviate the existing symptoms of the subject being treated without including unacceptable side effects. Determination of the effective amount is well within the capability of those skilled in the art, especially in light of the detailed disclosure provided herein. Toxicity and therapeutic efficacy of such compounds can be determined by standard pharmaceutical procedures in cell cultures or experimental animals, e.g., for determining the $LD_{50}$ (the dose lethal to 50% of the population) and $ED_{50}$ (the dose that provides 50% of the maximal response and/or is therapeutically effective in 50% of the population). The dosage can vary within this range depending upon the dosage form employed, and the route of administration utilized. The exact formulation, route of administration, and dosage is chosen by the individual physician in view of the patient's condition. Dosage amount and interval can be adjusted individually to provide plasma levels of the active compound that are sufficient to maintain desired therapeutic effects. In addition to the patient's condition and the mode of administration, the dose administered would depend on the severity of the patient's symptoms and the patient's age and weight. For example, for oral administration, the total daily dose range is 0.5-3 g/day. Preferably, the daily dose range is 1-2.5 g/day, while more preferably, the daily dose range is 1.5-2 g/day. Even more preferably, the daily dose range is 1.5-1.8 g/day. In one embodiment of the invention, the dose per day for oral administration is about 1.6 g/day. For intravenous administration, the dose range is 50-750 mg. Preferably, the dose range is 100-600 mg. More preferably, the dose range is 150-350 mg.

Even more preferably, the dose range is 175-325 mg. In one embodiment of the invention, the dose for intravenous administration is about 200 mg.

In accord with preferred embodiments of the invention, crystalline (+)-R-zileuton and the crystal forms of (+)-R-zileuton described herein are formulated for pharmaceutical administration to a subject including mammals, and preferably human beings. Pharmaceutical composition can be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. In one embodiment, the compositions are administered orally or intravenously.

Sterile injectable forms of compositions including crystalline (+)-R-zileuton and the crystal forms of (+)-R-zileuton described herein can be aqueous or oleaginous suspension. These suspensions can be formulated according to techniques known in the art using suitable dispersing or wetting agents and suspending agents. The sterile injectable preparation can also be a sterile injectable solution or suspension in non-toxic parenterally acceptable diluent or solvent, for example as a solution in 1,3-butanediol. Among the acceptable vehicles and solvents that can be employed are water, Ringer's solution, isotonic sodium chloride solution, dextrose. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in manufacture or pharmaceutically acceptable solid, liquid, or other dosage forms can also be used for the purpose of formulation.

Crystalline (+)-R-zileuton and the crystal forms of (+)-R-zileuton described herein, consistent with embodiments of the invention, can be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate or sodium stearyl fumarate, are also typically added. For oral administration in a capsule form, useful diluents include lactose and starch (e.g. dried cornstarch or pregelatinized starch). Other useful excipients include colloidal silicon dioxide, microcrystalline cellulose, and sucrose. When aqueous suspensions are required for oral use, the active ingredient is combined with emulsifying and suspending agents. If desired, certain sweetening, flavoring or coloring agents may also added.

Alternatively, crystalline (+)-R-zileuton and the crystal forms of (+)-R-zileuton described herein can be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

Crystalline (+)-R-zileuton and the crystal forms of (+)-R-zileuton described herein can also be administered topically, especially when the target of treatment includes areas or organs readily accessible by topical application, including disease of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches can also be used. For topical applications, crystalline (+)-R-zileuton and the crystal forms of (+)-R-zileuton described herein can be formulated in a suitable ointment containing the active component suspended or dissolved in one or more carriers. Carriers for topical administration of crystalline (+)-R-zileuton and the crystal forms of (+)-R-zileuton described herein include, but are not limited to, mineral oil, liquid petrolatum, white petrolatum, propylene glycol, polyoxyethylene, polyoxypropylene compound, emulsifying wax and water. Alternatively, crystalline (+)-R-zileuton and the crystal forms of (+)-R-zileuton described herein can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The particular crystalline form Form II of (+)-R-zileuton is prepared by solvent evaporation from a solution of (+)-R-zileuton in a solvent or a solvent mixture. The solvents that may be used include acetone, acetonitrile, ethyl acetate, and methyl tertiary-butyl ether (referred to as "MTBE" herein). Suitable solvent mixtures include an azeotropic mixture of acetone and heptane, an azeotropic mixture of acetonitrile and toluene, a 1:1 mixture of acetonitrile and water, an azeotropic mixture of ethanol and toluene, a 1:1 mixture of MeOH and water, and a 1:1 mixture of tetrahydrofuran and water.

In another embodiment of the invention, particular crystalline forms of (+)-R-zileuton are prepared from a slurry of (+)-R-zileuton in a solvent. Solvents that may be used are dichloromethane, toluene and water.

In another embodiment of the invention, the particular crystalline form Form II of (+)-R-zileuton is prepared through rapid cooling of a heated solution of (+)-R-zileuton in a solvent, by placing the solution in an cooling bath. Suitable solvents include ethyl acetate and MTBE.

In another embodiment of the invention, Form II of (+)-R-zileuton is prepared by adding a solution of (+)-R-zileuton in a solvent to an anti-solvent at a given temperature. More particularly, the anti-solvent is hexane.

As used herein, "anti-solvent" refers to a solvent, in which (+)-R-zileuton has low solubility.

EXPERIMENTAL

Crystallization Techniques

Evaporation Method. (+)-R-zileuton was dissolved in a given solvent and the resulting solution was filtered through a 0.2-μm filter. The solution was then left under ambient conditions or under nitrogen either in an open vial (fast evaporation) or in a loosely capped vial or a vial covered with aluminum foil containing pinholes (slow evaporation). The resulting solids were analyzed by light microscopy and XRPD.

Slurry Method. (+)-R-zileuton was added to a given amount of solvent until solids were present. The resulting mixture was placed on a rotating wheel at ambient temperature or in an orbital shaker set at 50° C. After several days, solids were isolated by centrifugation, followed by solvent decantation. The resulting solids were analyzed by light microscopy and XRPD.

Rapid Cooling Method. (+)-R-zileuton was dissolved in a single solvent or a solvent mixture by heating to 60° C. The solution was immediately filtered through a 0.2-μm filter into an open vial. Solid formation was induced by placing the vial into a cooling bath containing dry ice and isopropyl alcohol. Samples were then placed in a refrigerator or freezer or allowed to sit at ambient conditions in order to induce additional solid formation. The resulting solids were isolated through centrifugation, followed by solvent decantation. Solids were analyzed by light microscopy and XRPD.

Anti-Solvent Method. A solution of (+)-R-zileuton in a given solvent was added to an appropriate anti-solvent at a given temperature to induce solid formation. Samples were then placed in a refrigerator or freezer or allowed to sit at ambient conditions to induce additional solid precipitation. The resulting solids were isolated through centrifugation, followed by solvent decantation. Solids were analyzed by light microscopy and XRPD.

X-Ray Powder Diffraction

X-ray powder diffraction patterns for the samples were acquired on an INEL XRG-3000 diffractometer equipped with a curved position sensitive (CPS) detector with a 2θ range of 120°. The instrument was calibrated using a silicon reference standard. The tube voltage and amperage were set to 40 kV and 30 mA, respectively. The monochromomator slit was set at 5 mm by 160 μm. Samples were packed in glass XRPD-quality capillaries. Each capillary was mounted onto a goniometer head that is motorized to permit rotation of the capillary during data acquisition. Real time data were collected using Cu Kα radiation at a resolution of 0.03° for 2θ angles. Only data points within the 2θ range of 2.5-40° were displayed in the plotted XRPD patterns.

Differential Scanning Calorimetry

Differential scanning calorimetry (DSC) data was collected on a TA Instruments 2920 differential scanning calorimeter. Each sample was placed into an aluminum DSC pan, and the weight was accurately recorded. The pan was covered with a lid and crimped. For standard DSC, the sample cell was equilibrated at 25° C. and heated at a rate of 10° C. per minute between 25° C. and 350° C. A nitrogen purge was maintained over the sample during a scan.

Thermal Gravimetric Analysis

Thermal gravimetric analysis (TGA) data was collected on a TA Instruments 2950 thermogravimetric analyzer, calibrated with Nickel and Alumel™. Each sample was placed in an aluminum sample pan and inserted into the TGA furnace. The sample was first equilibrated at 25° C., and then heated under nitrogen flow at a rate of 10° C. per minute up to a final temperature of 350° C.

Moisture Sorption/Desorption Analysis

Moisture sorption/desorption data were collected on a VTI SGA-100 Vapor Sorption Analyzer, calibrated using sodium chloride and polyvinylpyrrolidone as calibration standards. Sorption and desorption data were collected over a range of 5% to 95% relative humidity (RH) at 10% RH interval under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the sample.

Hot Stage Microscopy

Hot stage microscopy was performed using a Linkam hot stage (model FTIR 600) mounted on a Leica DM LP microscope equipped with a Sony DXC-970MD 3CCD camera for image collection. Cross polarizers, a 20× objective and a first order red compensator were utilized to view samples. Samples were placed between two coverslips and run neat. Images were captured using SPOT v3.5.8. The hot stage was calibrated using USP melting point standards.

Single Crystal Structure Determination

Single crystals of Form II of (+)-R-Zileuton were prepared by solvent evaporation of a solution of (+)-R-Zileuton in a 1:1 solvent mixture of water and methanol. Suitable crystal with an approximate dimension of 0.48×0.30×0.08 mm was mounted on a glass fiber in random orientation. Preliminary examination and data collection were performed with Mo Kα (λ=0.71073 Å) radiation on a Nonius Kappa CCD diffractometer. Refinement were performed on an LINUX PC using SHELX97. The crystallographic drawings were obtained using the programs ORTEP, CAMERON and Mercury. Cell constants and an orientation matrix for data collection were obtained from least-square refinement using the setting angles of 24295 reflections in a range of 1°<θ<25°. The space group was determined by the program XPREP. The data were collected to a maximum 2θ value of 50.08° at a temperature 150±1 K.

The frames were integrated with DENZO-SMN. A total of 24295 reflections were collected, of which 7341 were unique. Lorentz and polarization corrections were applied to the data. The structure was solved by direct method using SIR2002. The remaining atoms were located in succeeding difference Fourier syntheses. Hydrogen atoms were included in refinement but restrained to ride on the atom to which they are bonded. The structure was refined in full-matrix least-squares by minimizing the function:

$$\Sigma w(|F_o|^2 - |F_c|^2)^2$$

where the weight w is defined as $1/[\sigma^2(F_o)^2+(0.0311\ P)^2+(0.0000P)]$ and P is defined as $(F_o^2+2F_c^2)/3$.

Scattering factors were taken from the "International Tables for Crystallography". Of the 7341 reflections used in the refinements, only the reflections with $F_o^2 > 2\sigma(F_o^2)$ were used in calculating R. A total of 4145 reflections were used in the calculation. The final cycle of refinement included 610 variable parameters and converged (largest parameter shift was essentially equal to its estimated standard deviation) with unweighted and weighted agreement factors of:

$$R=\Sigma|F_o-F_c|/\Sigma F_o \text{ and } R_w=\sqrt{(\Sigma w(F_o^2-F_c^2)^2/\Sigma w(F_o^2)^2)}$$

Preparation of Form I of (+)-R-Zileuton

Approximately 6 g of R-zileuton in approximately 12 L methanol was concentrated to dryness by portion using the rotary evaporator. After removing the residual solvent using high vacuum, a white solid (Form I of R-zileuton, >99% ee) was obtained.

Preparation of Form II of (+)-R-Zileuton

Form II of R-zileuton was prepared by recrystallization of Form I obtained above. About 200 mg Form I of R-zileuton was recrystallized from a minimum volume of hot acetonitrile to yield Form II of R-zileuton.

Form II can additionally be obtained using other crystallization methods described herein. For example, Form II can be obtained subjecting Form I of R-zileuton to fast evaporation from acetone.

While this invention has been particularly shown and described with references to embodiments thereof, it will be understood by those skilled in the art that various changes in form and details may be made therein without departing from the scope of the invention encompassed by the appended claims.

What is claimed is:

1. A composition comprising (+)-R-zileuton represented by the following structural formula:

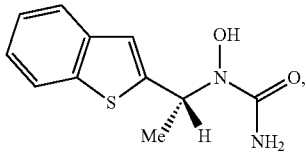

wherein at least 70% by weight of the composition is the single crystalline form Form I of (+)-R-zileuton, characterized by major x-ray powder diffraction peaks at 2θ angles of 4.5°, 9.1°, 16.3°, 17.3°, 17.9°, 20.3°, 22.2° and 24.0°.

2. The composition of claim 1, wherein the single crystalline form is characterized by x-ray powder diffraction peaks at 2θ angles of 4.5°, 9.1°, 16.3°, 17.3°, 17.9°, 20.3°, 22.2°, 22.7° and 24.0°.

3. The composition of claim 1, wherein the single crystalline form is characterized by x-ray powder diffraction pattern of FIG. 1.

4. The composition of claim 1, wherein the single crystalline form is characterized by a single endothermic transition at 151° C. in the differential scanning calorimetry profile with a scanning rate of 10° C./minute or the single crystalline form is anhydrous.

5. A pharmaceutical composition comprising a pharmaceutically acceptable carrier or diluent and the composition of claim 1.

6. The pharmaceutical composition of claim 1, wherein the single crystalline form is characterized by x-ray powder diffraction peaks at 2θ angles of 4.5°, 9.1°, 16.3°, 17.3°, 17.9°, 20.3°, 22.2°, 22.7° and 24.0°.

7. The pharmaceutical composition of claim 1, wherein the single crystalline form is characterized by x-ray powder diffraction pattern of FIG. 1.

8. The pharmaceutical composition of claim 1, wherein the single crystalline form is characterized by a single endothermic transition at 151° C. in the differential scanning calorimetry profile with a scanning rate of 10° C./minute or the single crystalline form is anhydrous.

9. The pharmaceutical composition of claim 5 wherein at least 99% by weight of the (+)-R-zileuton is the single crystalline form.

10. The pharmaceutical composition of claim 5 wherein at least 99.9% by weight of the (+)-R-zileuton is the single crystalline form.

11. A composition comprising (+)-R-zileuton represented by the following structural formula:

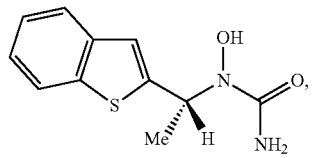

wherein at least 70% by weight of (+)-R-zileuton is a single crystalline form Form II of (+)-R-zileuton characterized by major x-ray powder diffraction peaks at 2θ angles of 4.6°, 9.2°, 16.1°, 16.3°, 17.6°, 18.6°, 19.9°, 21.3°, 23.4° and 23.7°.

12. The composition of claim 11, wherein the single crystalline form is characterized by x-ray powder diffraction pattern of FIG. 4.

13. A pharmaceutical composition comprising a pharmaceutically acceptable carrier or diluent and the composition of claim 11.

14. The pharmaceutical composition of claim 13, wherein the single crystalline form is characterized by x-ray powder diffraction pattern of FIG. 4.

15. A method of treating asthma or nasal polyposis in a subject in need thereof comprising administering to the subject an effective amount of a pharmaceutical composition comprising a pharmaceutically acceptable carrier or diluent and (+)R-zileuton represented by the following structural formula:

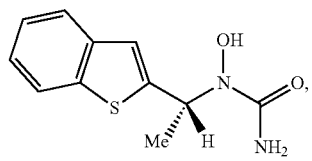

wherein at least 70% by weight of the (+)-R-zileuton is crystalline Form I of (+)-R-zileuton characterized by major x-ray powder diffraction peaks at 2θ angles of 4.5°, 9.1°, 16.3°, 17.3°, 17.9°, 20.3°, 22.2° and 24.0°, or crystalline Form II of (+)-R-zileuton characterized by major x-ray powder diffraction peaks at 2θ angles of 4.6°, 9.2°, 16.1°, 16.3°, 17.6°, 18.6°, 19.9°, 21.3°, and 23.4°.

* * * * *

UNITED STATES PATENT AND TRADEMARK OFFICE
CERTIFICATE OF CORRECTION

Page 1 of 1

PATENT NO. : 8,003,684 B2
APPLICATION NO. : 11/709299
DATED : August 23, 2011
INVENTOR(S) : Jason A. Hanko It is certified that error appears in the above-identified patent and that said Letters Patent is hereby corrected as shown below:

In the claims:

Column 15, line 30, claim 4, "151° C. in" should be changed to --151° C in--

Column 15, line 31, claim 4 "10° C./minute" should be changed to --10° C/minute--

Column 15, line 36, claim 6 "claim 1" should be changed to --claim 5--

Column 15, line 40, claim 7 "claim 1" should be changed to --claim 5--

Column 15, line 43, claim 8 "claim 1" should be changed to --claim 5--

Column 15, line 45, claim 8 "151° C. in" should be changed to --151° C in--

Column 15, line 46, claim 8 "10° C./minute" should be changed to --10° C/minute--

Signed and Sealed this
Sixth Day of March, 2012

David J. Kappos
*Director of the United States Patent and Trademark Office*